(12) United States Patent
Harding et al.

(10) Patent No.: US 10,857,538 B2
(45) Date of Patent: Dec. 8, 2020

(54) SAMPLE PREPARATION SYSTEM AND CARTRIDGE

(71) Applicant: TTP Plc, Royston (GB)

(72) Inventors: Piers Sebastian Harding, Royston (GB); Gary Stephen Howard, Royston (GB); Gary Keith Jepps, Royston (GB)

(73) Assignee: TTP Plc, Royston (GB)

( * ) Notice: Subject to any disclaimer, the term of this patent is extended or adjusted under 35 U.S.C. 154(b) by 262 days.

(21) Appl. No.: 15/780,814

(22) PCT Filed: Dec. 5, 2016

(86) PCT No.: PCT/GB2016/053817
§ 371 (c)(1),
(2) Date: Jun. 1, 2018

(87) PCT Pub. No.: WO2017/093763
PCT Pub. Date: Jun. 8, 2017

(65) Prior Publication Data
US 2019/0270086 A1    Sep. 5, 2019

(30) Foreign Application Priority Data

Dec. 4, 2015 (GB) .................................. 1521418.2
Mar. 8, 2016 (GB) .................................. 1603938.0

(51) Int. Cl.
*B01L 7/00* (2006.01)
*C12N 15/10* (2006.01)
(Continued)

(52) U.S. Cl.
CPC ............ *B01L 7/52* (2013.01); *C12N 15/1003* (2013.01); *G01N 35/0098* (2013.01);
(Continued)

(58) Field of Classification Search
CPC .............................. B01L 7/52; G01N 35/0098
See application file for complete search history.

(56) References Cited

U.S. PATENT DOCUMENTS

2010/0192706 A1*  8/2010  Fairs .................. G01N 1/28
                                              73/863.23
2010/0261179 A1* 10/2010  Betley ................. B03C 1/288
                                              435/6.11

FOREIGN PATENT DOCUMENTS

WO    2012094625 A2    7/2012

OTHER PUBLICATIONS

International Search Report dated Jul. 31, 2017, in International Application No. PCT/GB2016/053817; Filed: Dec. 5, 2016; Applicant: The Technology Partnership PLC.
(Continued)

*Primary Examiner* — Matthew D Krcha
(74) *Attorney, Agent, or Firm* — Erise IP, P.A.

(57) ABSTRACT

A sample preparation cartridge for use with a sample preparation device, the cartridge includes a housing defining plural separate segments, at least one of said segments comprising a fixed section of a pipette component; and a moveable head comprising a pipette tip, the head being configured, in use, to be moved between a position in which the pipette tip is in sealed engagement with the fixed section of pipette component and a position in which pipette tip is positioned adjacent to another of said plural segments. With the present invention a disposable sample preparation cartridge and corresponding analytical reader can be provided in a very cost effective and simple manner whilst still ensuring high quality sample preparation for analysis.

20 Claims, 15 Drawing Sheets

(51) Int. Cl.
*G01N 35/10* (2006.01)
*G01N 35/00* (2006.01)
*G01N 35/04* (2006.01)
*B01L 3/00* (2006.01)
*B01L 3/02* (2006.01)

(52) U.S. Cl.
CPC ..... *G01N 35/1079* (2013.01); *G01N 35/1083* (2013.01); *B01L 3/021* (2013.01); *B01L 3/545* (2013.01); *B01L 2200/04* (2013.01); *B01L 2200/0647* (2013.01); *B01L 2200/0684* (2013.01); *B01L 2200/141* (2013.01); *B01L 2300/021* (2013.01); *B01L 2300/022* (2013.01); *B01L 2300/043* (2013.01); *B01L 2300/044* (2013.01); *B01L 2300/0672* (2013.01); *B01L 2300/0681* (2013.01); *B01L 2300/0841* (2013.01); *B01L 2300/0867* (2013.01); *B01L 2300/0887* (2013.01); *B01L 2400/0421* (2013.01); *G01N 35/00732* (2013.01); *G01N 2035/00465* (2013.01); *G01N 2035/0403* (2013.01); *G01N 2035/0436* (2013.01)

(56) References Cited

OTHER PUBLICATIONS

Written Opinion of the International Searching Authority dated Jul. 31, 2017, in International Application No. PCT/GB2016/053817; Filed: Dec. 5, 2016; Applicant: The Technology Partnership PLC.

* cited by examiner

1

1

SAMPLE PREPARATION SYSTEM AND CARTRIDGE

RELATED APPLICATIONS

The present application is a national stage application under 35 U.S.C. § 371 of International Application No. PCT/GB2016/053817, filed 5 Dec. 2016, which claims priority to Great Britain Patent Application No. 1603938.0, filed 8 Mar. 2016, and Great Britain Patent Application No. 1521418.2, filed 4 Dec. 2015. The above referenced applications are hereby incorporated by reference into the present application in their entirety.

FIELD

The present invention relates to a sample preparation system with a sample preparation cartridge and an analytical reader.

In the field of diagnostics there has been a growing need to provide sample preparation devices that can be used in the analysis of a sample from a patient. In particular there is a growing need for Point of Care diagnostic devices that enable a sample to be prepared and analysed at the location of the patient to ensure rapid analysis and improve overall care for a patient.

The Point of Care diagnostics market has been growing for several years with the ultimate goal of fulfilling the promise of personalised medicine, or providing the right therapy at the right time for the right patient. Many analytical approaches can be applied to samples, such as a molecular diagnostics, chemical analysis, immunoassays, and flow cytometry. Current systems typically manipulate samples using a predetermined sequential process of fluid manipulation through chambers according to a specific protocol and as such are not very versatile.

Accordingly, there is a need to supply the sample to the analytical device in a safe and reliable manner whilst providing an automated but flexible method comprising a readily programmable series of processing steps. There is furthermore a need to provide a sample preparation cartridge which is small in size and weight, as well as being easy to manufacture and of low cost. There is also a need for the analytical reader to be easy to use whilst still ensuring accurate and reliable analytical results.

SUMMARY

The present invention seeks to at least partially address some of the above problems.

According to the present invention there is provided a sample preparation cartridge for use with a sample preparation device, the cartridge comprising: a housing defining plural separate segments, at least one of said segments comprising a fixed section of a pipette component; and a moveable head comprising a pipette tip, the head being configured, in use, to be moved between a position in which the pipette tip is in sealed engagement with the fixed section of pipette component and a position in which pipette tip is positioned adjacent to another of said plural segments.

With the present invention a disposable sample preparation cartridge and corresponding analytical reader can be provided in a very cost effective and simple manner whilst still ensuring high quality sample preparation for analysis. The described two part pipette configuration (comprising a fixed section and a nozzle or tip) provides a highly flexible and compact approach that can be realised in a portable system or a bench top instrument. The sample preparation cartridge is easy to fill and seal, as well as being compact and having a low weight. It is also easy for an unskilled user to operate. In addition, the sample preparation cartridge is arranged to be received into, or onto, an analytical reader constructed simply with few moving components whilst still ensuring high quality sample preparation.

Furthermore, with the sample preparation cartridge according to the present invention, a sample may be easily and safely transferred selectively between segments (which may also be referred to as chambers), whilst ensuring it remains sealed within the cartridge. This allows a sequence of processing steps to be selected and performed by configuring the series of segments between which a sample is transported.

The invention can be used to provide an apparatus for analysing a fluid sample by separating and holding a desired analyte, for chemical reaction, from a biological fluid sample. In a preferred use the analyte is nucleic acid, but could also be proteins, carbohydrates, bacteria or parasites.

The system is also capable of processing samples such as blood, saliva, urine, mucus or other bodily fluids as well as solid samples or airborne particles suspended in a liquid. Some samples can be presented to the apparatus in a raw form whilst others may be pre-mixed with chemicals, reagents, diluents or buffers or pre-treated with centrifuge, sonicators, macerators, etc.

When the desired analyte is nucleic acid such as DNA or RNA, the cartridge will separate the nucleic acid from the sample, purify it by washing and then hold it for amplification using PCR. Detection is achieved using optical or electrochemical methods.

An alternative cartridge comprising a single-piece pipette structure is able to exploit the flexibility, low weight and ease of use benefits, albeit at the cost of a higher profile cartridge.

Examples of the present invention will now be described with reference to the accompanying drawings in which.

Figure 1:
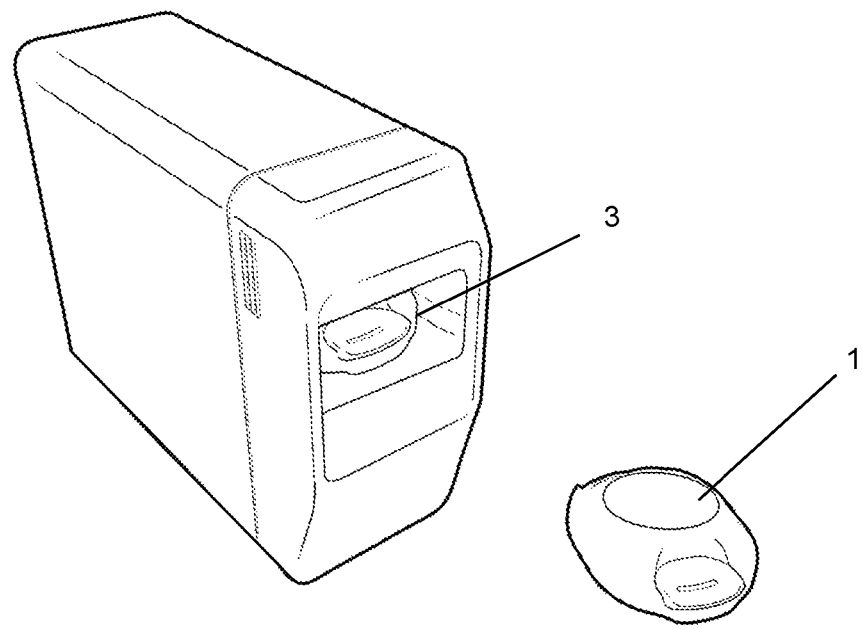
FIG. 1 is a schematic view of a system according to the present invention including a sample preparation cartridge and sample preparation device.

FIG. 1 depicts a system for analysing fluid samples comprising a removably insertable cartridge 1 and a sample preparation instrument including an analytical reader 3. The ornamental design of the cartridge 1 and instrument 3 can be varied without impacting the performance of the system, however features of the current invention disclosed herein enable the cartridge 1 to have a low profile and thus enable the overall combination of cartridge and instrument to be extremely compact. The separation of the system into cartridge and instrument enables a multitude of tests, configured within specific cartridges, to be automatically undertaken with a single instrument. These include, but are limited to PCR (thermally cycled), PCR (isothermal), immunoassay, clinical chemistry and lateral flow.

Figure 2:
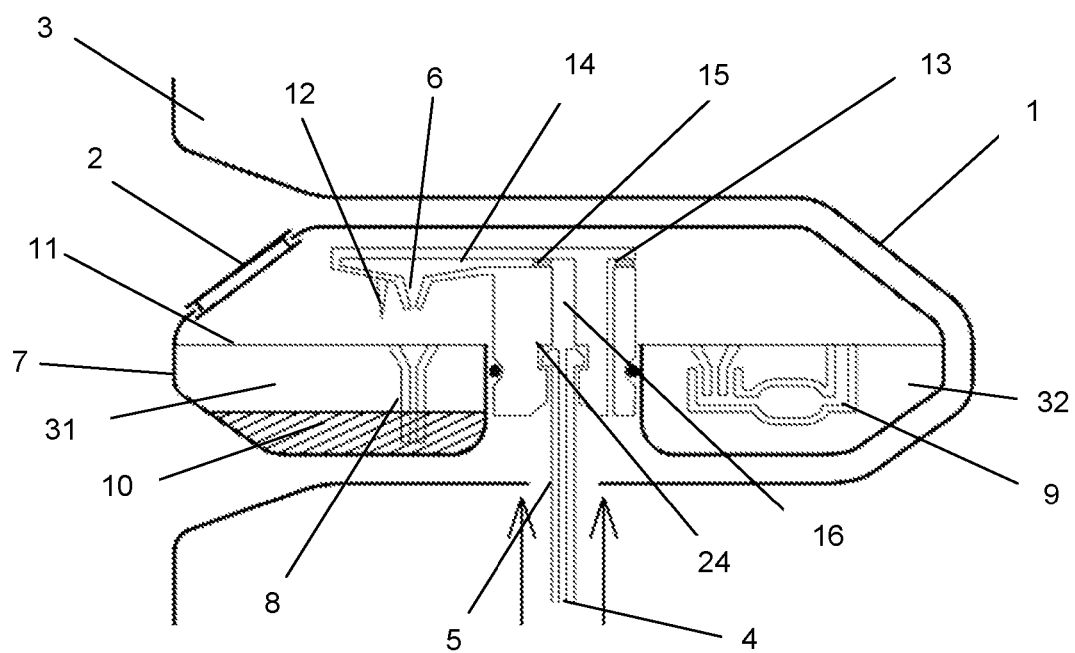
FIG. 2 is a side schematic cross-sectional view of a sample preparation cartridge according to the present invention when inserted into the analytical reader of a sample preparation device.
Figures 3A, 3B:
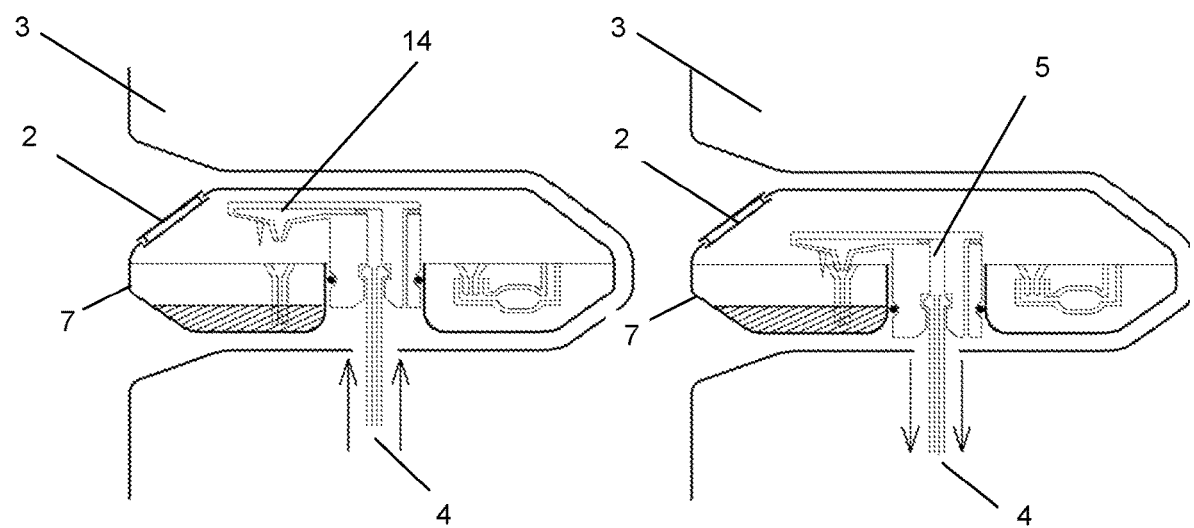
FIGS. 3a and 3b are side schematic cross-sectional views of the sample preparation cartridge of FIG. 2 showing raised and lowered pipette configurations respectively.

Referring to FIG. 2, a sample preparation cartridge 1 according to the present invention is a hollow sealed container having an outer shell 7. A closable door 2 in the shell 7 allows access via the user to insert a sample (not shown) into the cartridge 1 in use. The cartridge 1 can then be inserted into an analytical reader 3 of a sample preparation device in an opening therein.

Figure 4:
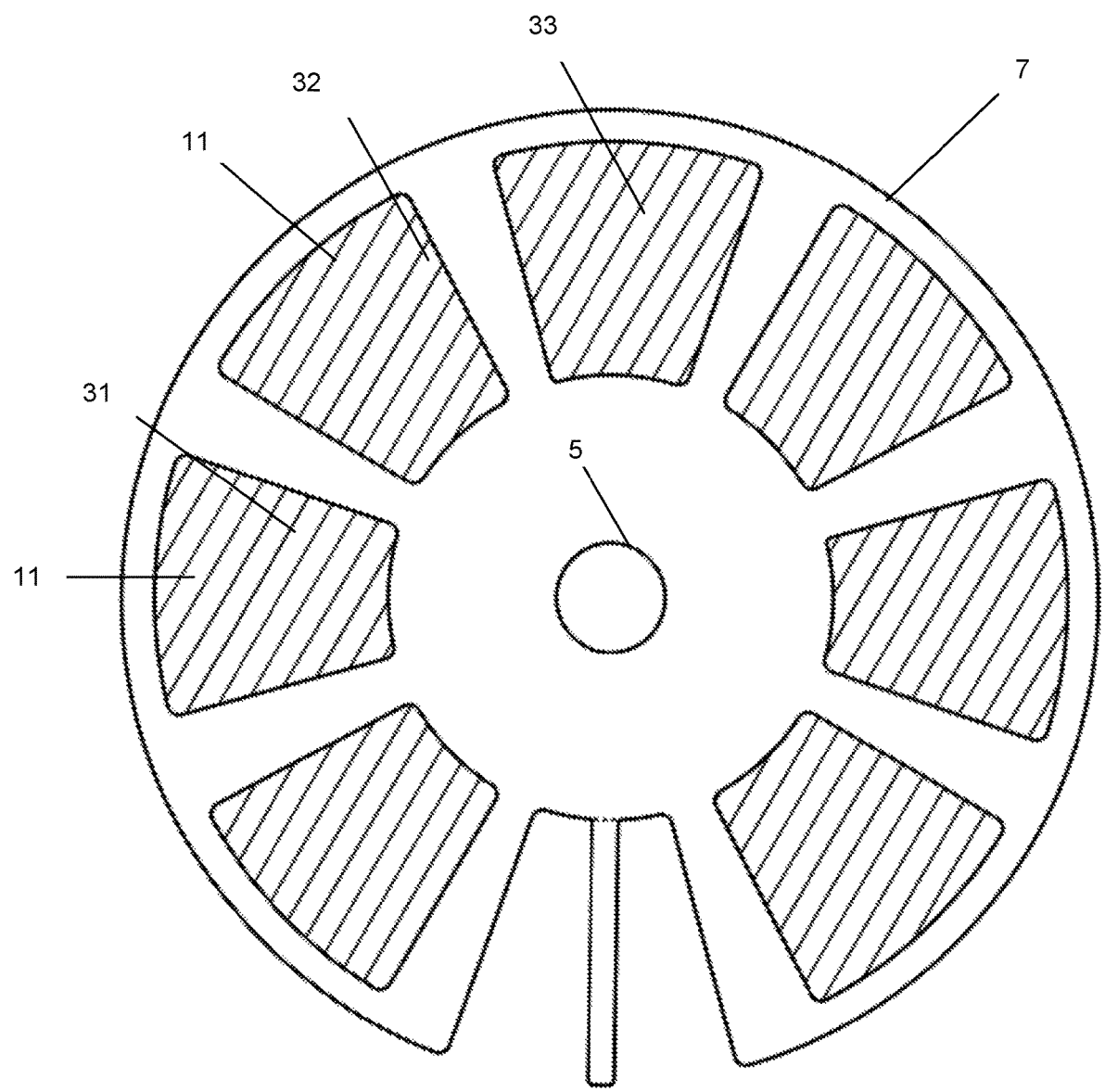
FIG. 4 is a plan schematic cross-sectional view of the sample preparation cartridge of the earlier figures.
Figure 5:
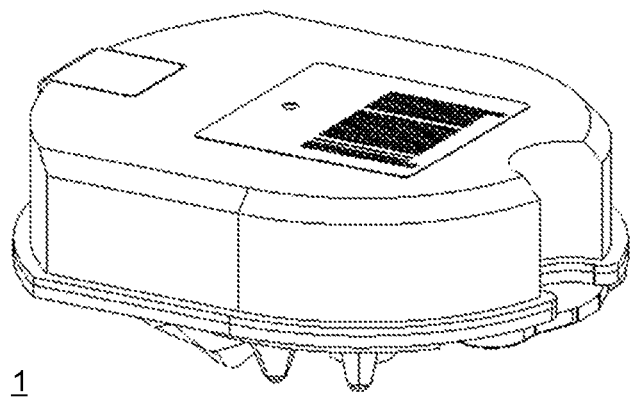
FIGS. 5 to 7 are perspective views of a cartridge according to the present invention, below and above with separable receiving port open respectively.
Figure 6:
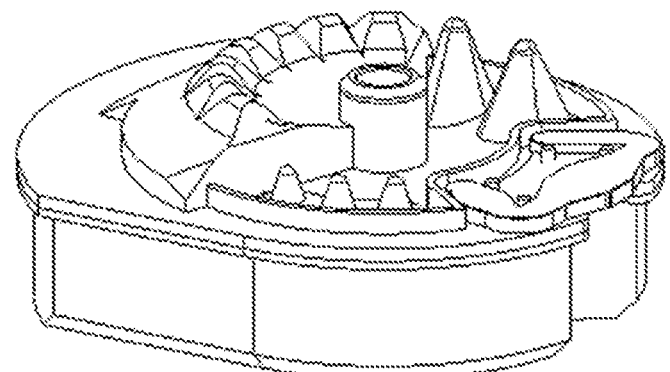
Figure 7:
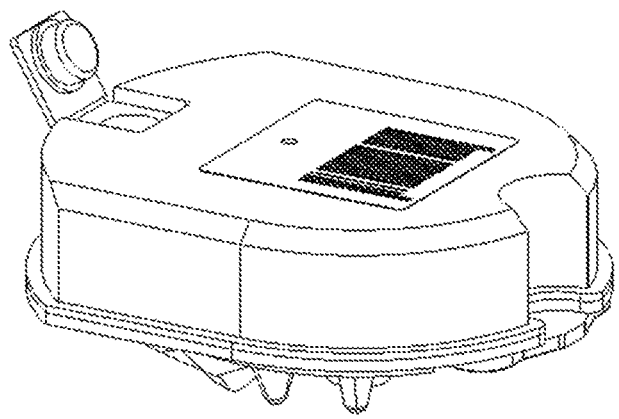
Figure 8:
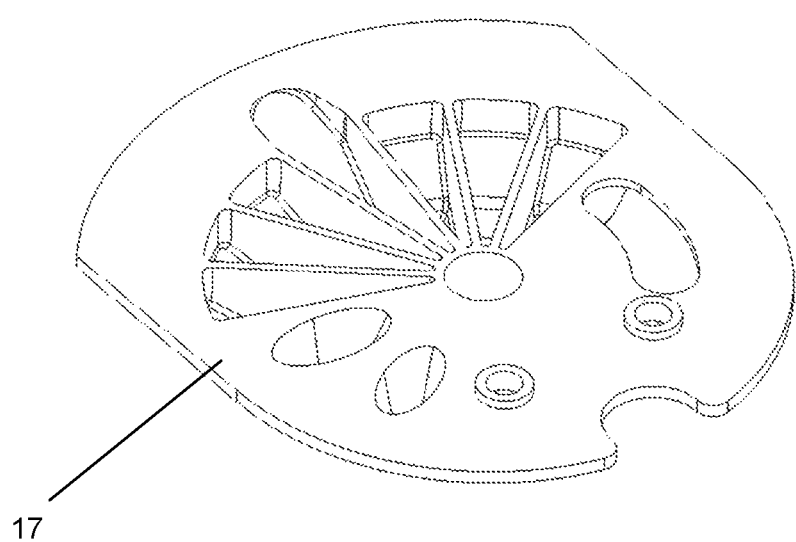
FIGS. 8 to 12 are views of components of the cartridge of FIGS. 5 to 7.
Figure 9:
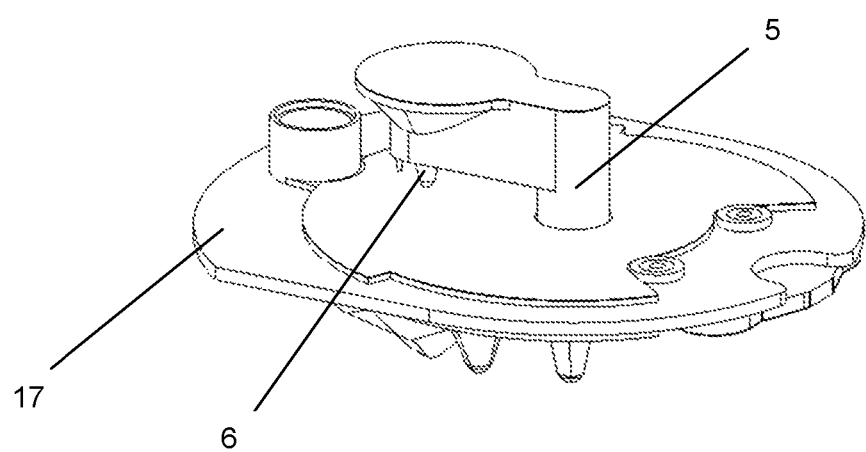
Figure 10:
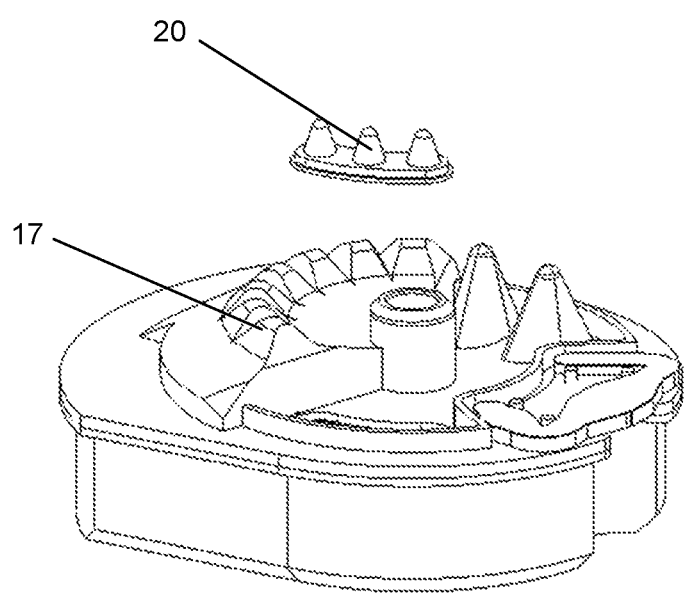
Figure 11:
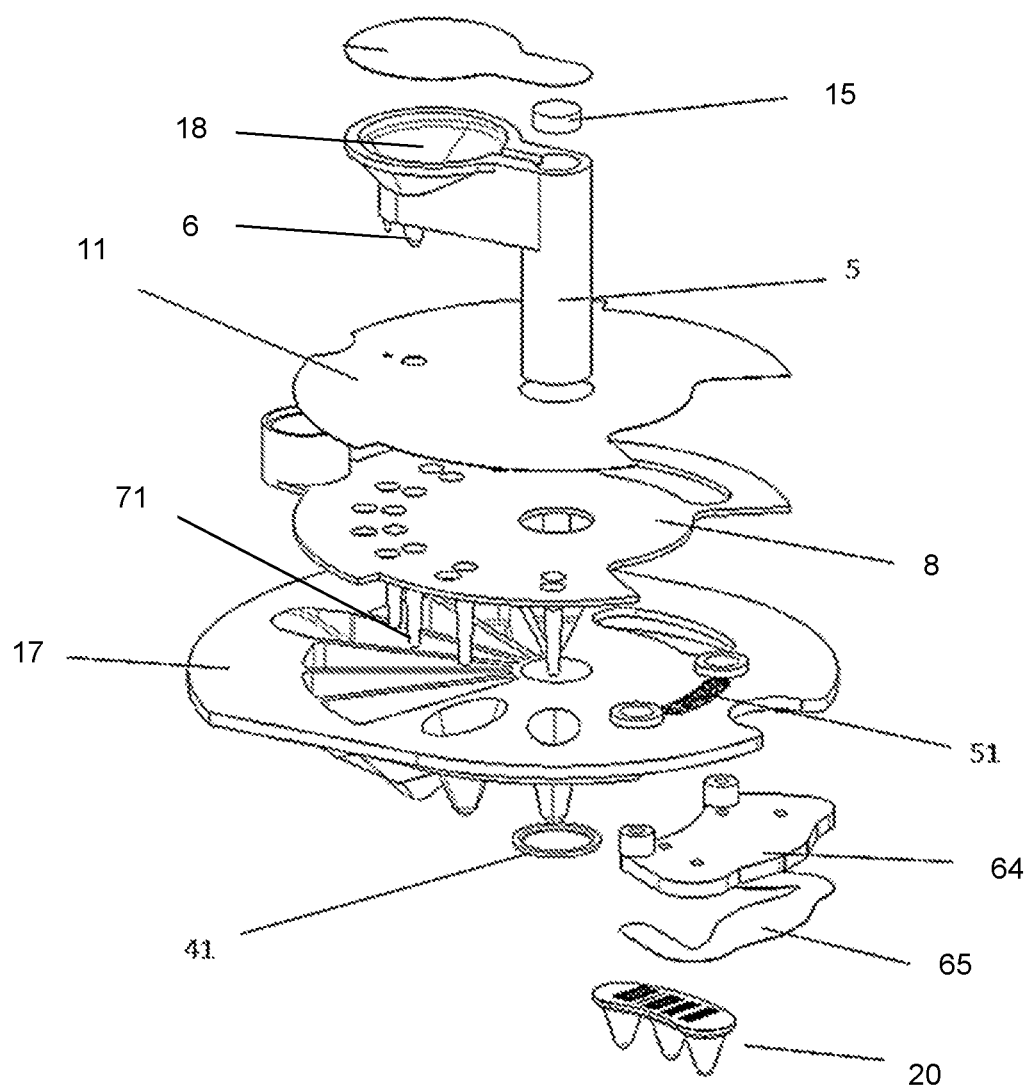
Figure 12:
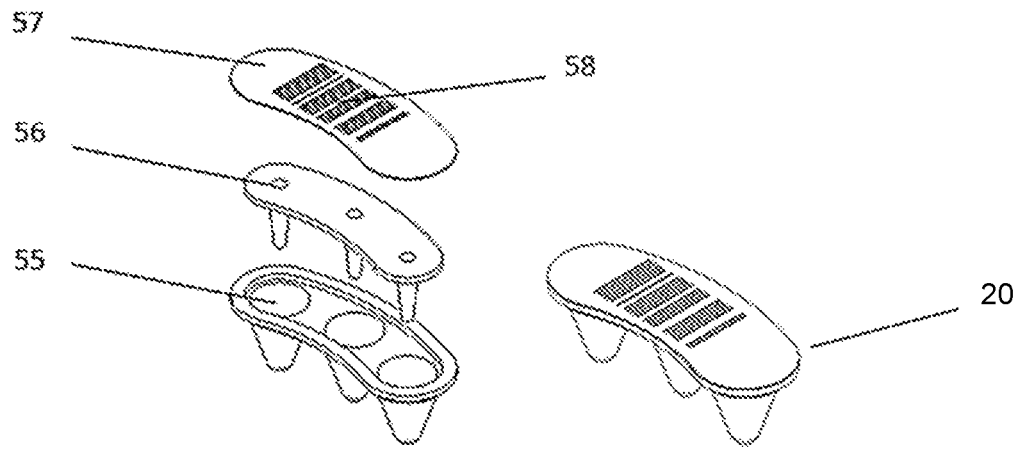
Figure 13:
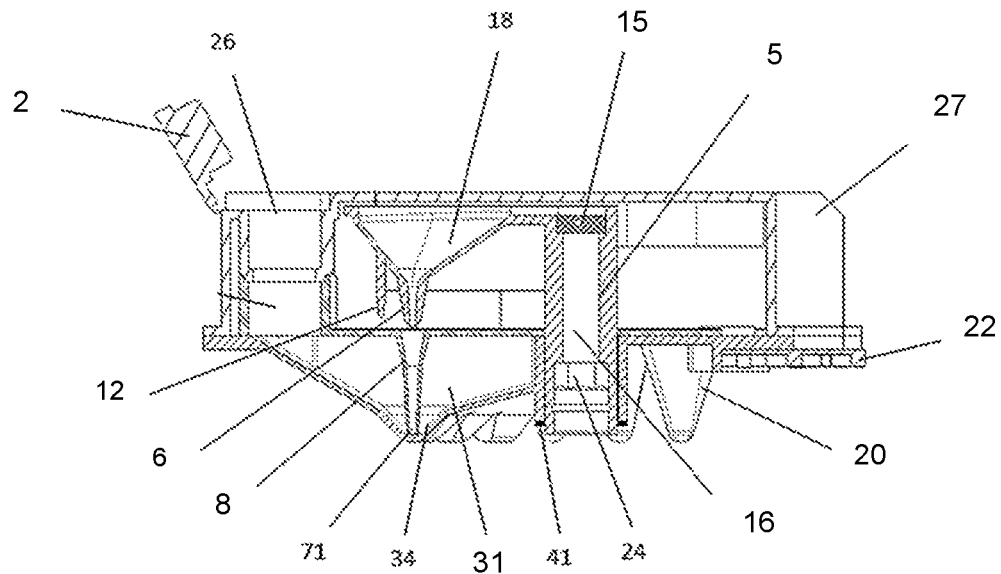
FIGS. 13 to 15 are side cross-sectional views of the cartridge.
Figure 14:
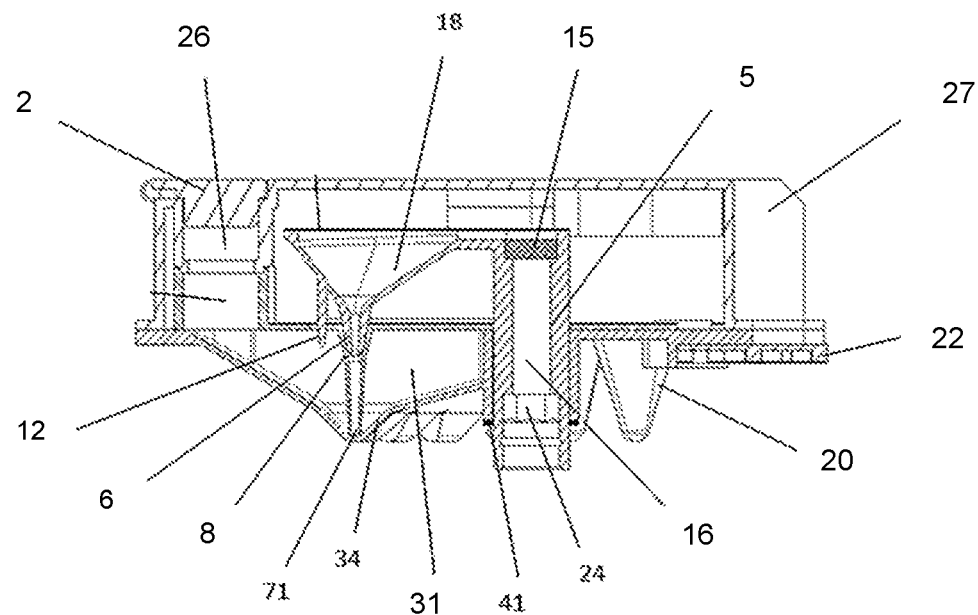
Figure 15:
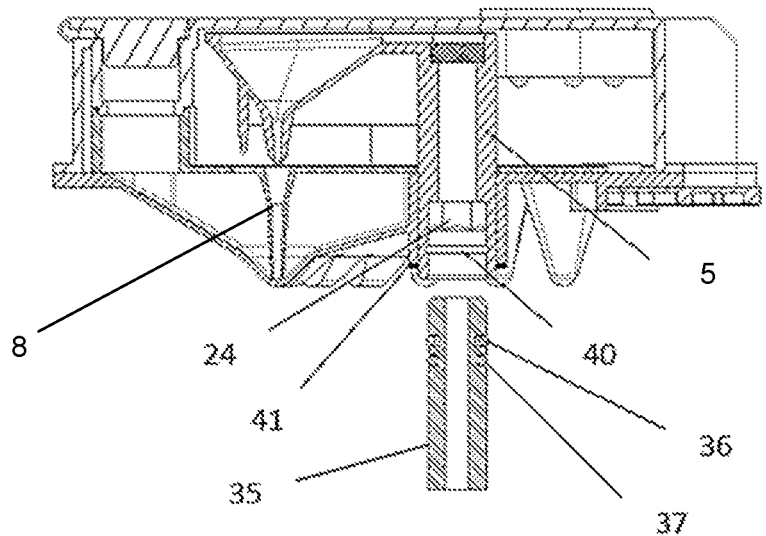
Figure 16:
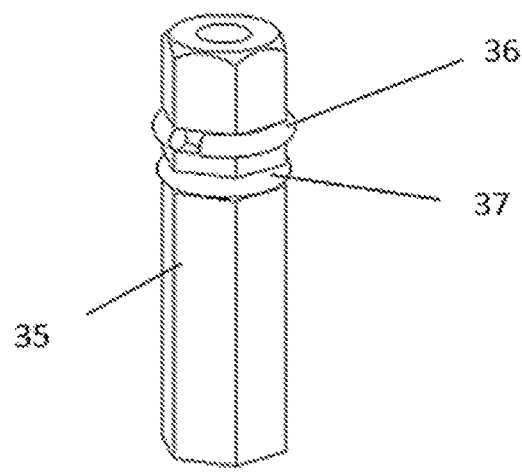
FIG. 16 shows a side perspective view of a drive shaft for use with the invention.
Figure 17:
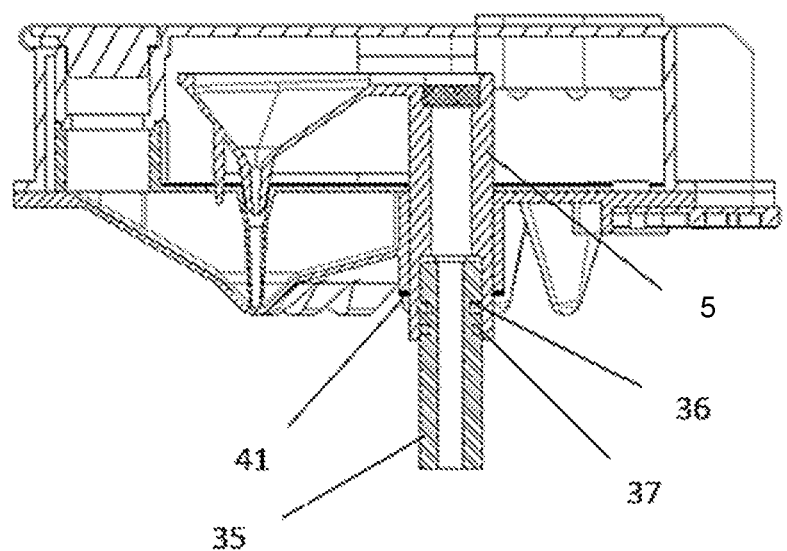
FIG. 17 shows the cartridge of the invention engaging with the drive shaft of FIG. 16.
Figure 18:
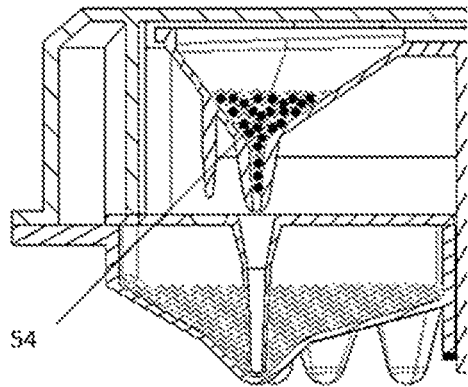
FIGS. 18 to 23 are side cross-sectional views of different components of the invention during operation with a liquid containing magnetic particles.
Figure 19:
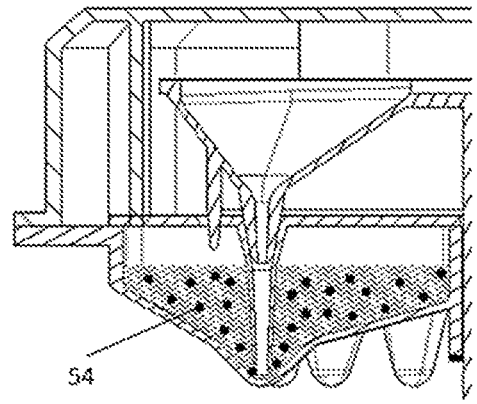
Figures 20, 21, 22:
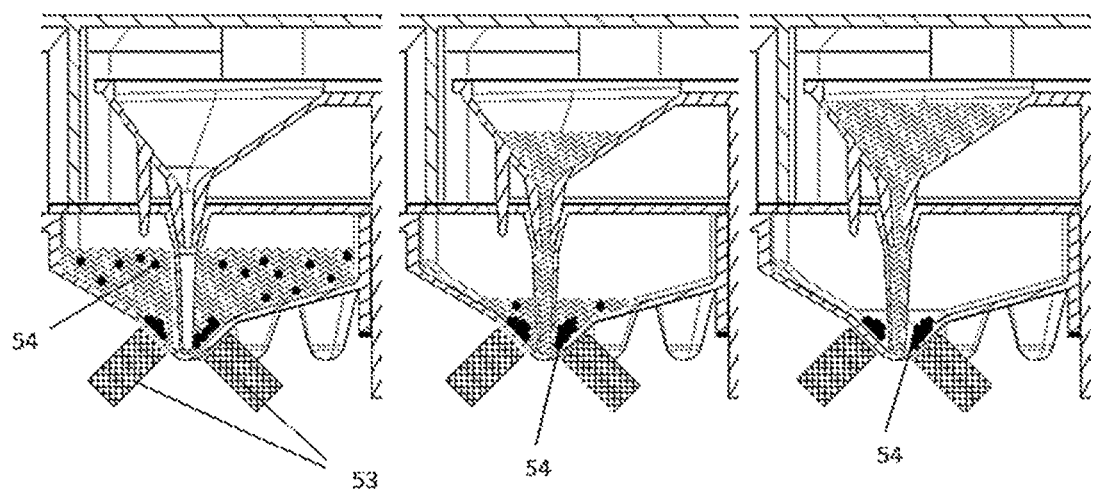
Figure 23:
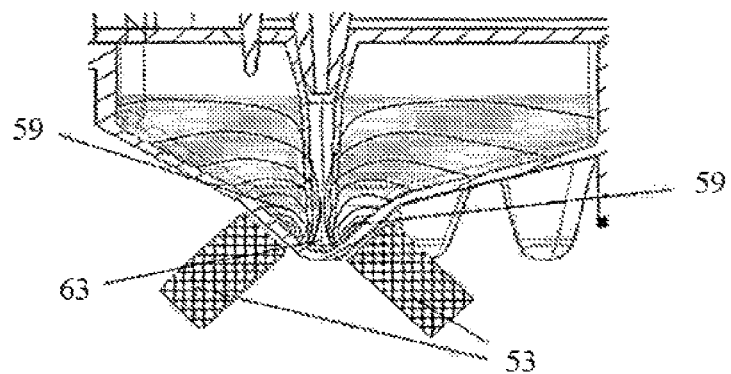
Figure 24:
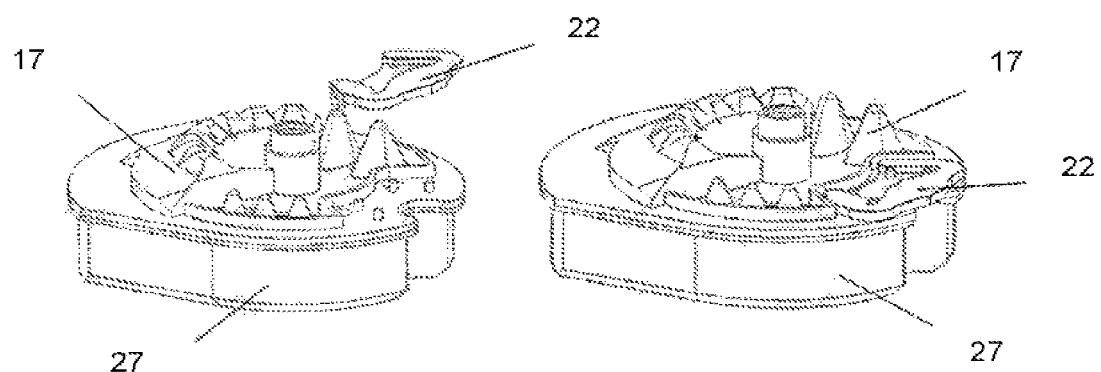
FIGS. 24, 25 and 26 show further optional components that may be employed in conjunction with a cartridge and system according to the invention.
Figure 25:
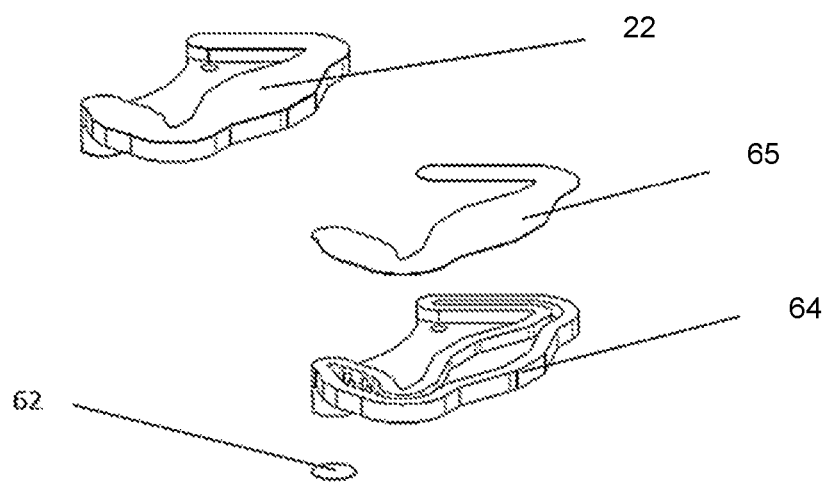
Figure 26:
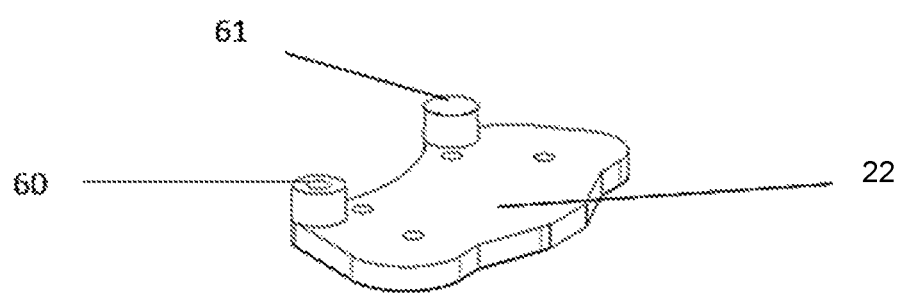

As can be seen from FIG. 4, the sample preparation cartridge 1 is divided into plural segments 31, 32, 33 each providing a chamber 31, 32, 33 which may contain substances for preparation, or components to aid in preparation or reading of the processed sample such as a cuvette 9, or a combination thereof. At least some segments 31, 32, 33 are sealed using a sealing member 11, that may be a foil sheet 11 to ensure that there is no contamination between individual segments 31, 32, 33 during the sample preparation cartridge's 1 handling and/or during its use within the analytical reader 3 of the sample preparation device.

As can also be seen in FIG. 4, the segments 31, 32, 33 are arranged around a central shaft 5 in a circular fashion around the central axis of the sample preparation cartridge 1. The central shaft 5 is arranged so that it can rotate with respect to the outer shell 7 of the sample preparation cartridge 1, and also so that it can slide in the axial direction of the sample preparation cartridge 1—the axial direction being perpendicular to the plane in which the chambers 31, 32, 33 are circularly arranged. However, during movement of the central shaft 5, it also maintains a seal between the exterior of the cartridge 1 and its interior. The shaft 5 has a passageway 16 in connection with pipette arm 14 with an open tip (which may also be referred to as a nozzle) 6 that passes through a filter component 15 and enables fluid access when required to the tip 6 via the shaft 5 to the exterior of the cartridge 1. An optional piercing component such as a spike 12 is provided to enable selective piercing of any seal member 11 when required. In addition, an optional venting shaft with a filtered valve 13 is provided in the shaft 5 to ensure equalization of pressure between the interior of the sample preparation cartridge 1 and the external atmosphere if necessary. Also provided in the pipette component of the central shaft 5 is a receiving component 24 which can receive, in use, a central drive member 4 from the sample preparation device 3 when the sample preparation cartridge 1 has been inserted therein. This central drive member 4 has a hollow core which can act to provide fluid connection and access to the passageway component 16 in the central shaft 5. When the drive member 4 is in engagement with the shaft 5 it can also act to move the shaft 5 in the axial direction of the sample preparation cartridge 1, thereby raising and lowering the pipette tip 6 with respect to the individual segments 31, 32, 33 within the shell 7. It can also rotate the shaft 5 around the sample preparation cartridge 1 to move the pipette tip 6 so it is positioned above a selected segment chamber 31, 32, 33.

When in the lowered position tip 6 engages and fluidly seals with the mouth of fixed part of the pipette 8 positioned within a segment 31, 32, 33.

In use the sample preparation cartridge 1 is opened by a user and a sample placed within the sample preparation cartridge 1 via the door 2. The door 2 is then closed and the sample preparation cartridge 1 is inserted into the analytical reader 3. The drive member 4 from the analytical reader 3 is raised to engage with the shaft 5 of the sample preparation cartridge 1. The pipette arm 14 can then be rotated to its desired position above a desired segment within the sample preparation cartridge 1. The pipette arm 14 can then be lowered, with the spike 12 piercing any sealing member 11 as lowering occurs, to provide a vent hole in the sealing 11 of the segment 31, 32, 33. Rotary movement of the pipette tip 6 at this stage will widen the spike hole to ensure that venting occurs. The pipette arm 14 and its tip 6 can then engage with any fixed section of pipette 8 in a particular segment 31, 32, 33. The tip 6 of the pipette engages with the fixed section of the pipette 8 in the segment to provide a fluid seal and allow any fluid 10 in the desired segment to be drawn up via the tip 6 into the pipette arm 14. The fluid can, if desired be drawn into the analytical reader of the sample preparation device 3, or may alternatively be held within the pipette arm 14 whilst it is then raised, rotated and lowered into another desired segment chamber 31, 32, 33 where further processing may occur. The other desired segment may contain other analytical substances, or as shown in FIG. 2, may have analytical components in there in which various substances can be mixed and reactions occur if necessary. Filtering using a filter 15 in the pipette can prevent any unwanted components passing into the core of the drive member 4 so that any subsequent sample that is introduced via a sample preparation cartridge 1 will not contaminate the analytical reader 3.

As will be appreciated, there are a number of sample preparation techniques and analytical approaches that the sample preparation cartridge 1 and analytical reader 3 of the sample preparation instrument according to the invention can be configured to follow dependent upon the information required in respect of an individual patient. In one example a sample can be provided which is then lysed and then mixed with paramagnetic particles to provide magnetic bead separation of target entities which will be described in more detail in reference to the further embodiments of the current invention below.

FIGS. 5 to 27 illustrate further examples of the present invention. In these examples the cartridge 1 comprises; a lower tray 17, for storing and processing the sample, an upper cover 27, a cuvette 9 and a moveable pipette tip 6. A port 26, in the upper cover 27, allows the user to introduce samples into the cartridge 1. A door 2 on the upper cover 27 can seal the sample within the cartridge 1 thus preventing contamination of the instrument 3. Other configurations, such as a membrane seal enabling sample insertion or a removable sample cassette comprised within an insertable bung that functions additionally as a door 2, are possible. However the use of a port 26 and a door 2 enables the sample to be inserted with minimum risk of contamination or sample fluid loss and at the same time reduces manufacturing complexity. The cartridge 1 may be manufactured as an assembly of components which may be individually moulded, milled, manufactured using additive assembly techniques or otherwise manufactured.

The lower tray 17 contains a plurality of formed segments 31, 32, 33 which provide chambers used to store, contain and process the sample. The geometry of each chamber 31, 32, 33 is preferably wedge or cone shaped, with a tapering 'V' shaped floor 34 so as to provide an effective drainage point to extract fluids 10. Chambers 31, 32, 33 can be covered by a breakable cover seal 11, such as a foil seal to prevent spillage in transit and increase the shelf life of the reagents. The upper cover 27 can carry a machine-readable identification coded tag, such as a 2D bar code 50, RFID chip or other optical, magnetic or near-field wireless interface for conveying data that can be read by the reader. The coded tag can convey data identifying the nature of the cartridge 1 and the assays, steps or tests contained therein. The coded tag can convey specific instructions to the analytical reader of the device 3. For example a cartridge 1 comprising a new test may be launched on the market after the introduction of the system and the coded tag can be used to advise the instrument 3 of specific temperature cycling requirements. Alternatively or additionally the coded tag may be used to advise the analytical reader of the instrument 3 of time periods, such as settling times during sample aspiration for example. The coded tag may further convey traceability and/or tracking information as well as other useful parameters such as expiry date. The data and instructions encoded on the coded tag may be used automatically by the instrument 3, and may be done so selectively either with or without user intervention, to deliver a number of enhanced system benefits, safety and efficacy warnings, and/or usability features. The coded tag 50 may incorporate active communication such that status or error messages can be conveyed between cartridge 1 and instrument 3.

After the sample is introduced and sealed within the cartridge 1, the cartridge 1 is inserted into the analytical reader of the sample preparation instrument 3 where a central drive shaft 35 of the drive member 4 of the analytical reader 3 is raised to mechanically and pneumatically engage with the movable pipette tip 6 via the shaft 5. The mechanical coupling is designed to allow the instrument to selectively move the pipette tip 6, and in this embodiment includes a hexagon shaped drive shaft 35 that locates into a tapering hexagonal hole 24 in the pipette's central shaft 5 so as to provide a means to transfer rotary and vertical motion to accurately control the position of the movable pipette 6. The hexagon arrangement allows for ease of engagement; however other shaft profile shapes could be used. The drive shaft 35 includes a split-ring 36 that locates in a recess 40 in the pipette central shaft 5 to provide a positive mechanical coupling during vertical movement of the shaft 5.

The coupling arrangement also includes an O-ring 37, mounted on the drive shaft 35 that pneumatically seals against the inside face of the pipette's central shaft 5 during engagement of the drive shaft 35 into the moveable pipette tip 6.

Alternative drive configurations are possible. For example, the drive shaft 35 may be incorporated within the cartridge 1, and a gear or set of teeth located at its lower edge to interlock with a complementary gear or teeth arrangement located within the instrument 3. Alignment sensors may be incorporated into the drive shaft 35, hole 24 or elsewhere that may be used to convey, via an active coded tag, the current status of the cartridge 1 to the analytical reader of the sample preparation instrument 3.

A movable pipette 6 is used to manipulate fluids within the chambers 31, 32, 33 in the lower tray 17. The pipette includes a moveable pipette tip 6, a reservoir 18, connected to a central shaft 5 and is selectively connected to a plurality of fixed pipette nozzle parts 8; one located in each chamber 31, 32, 33. The fixed nozzles 8 are positioned so that their tips 71 are at the lowest point of each chamber 31, 32, 33 to enable extraction of the maximum amount of fluid 10 from each chamber 31, 32, 33.

The geometry of the apparatus allows the instrument 3 to selectively determine the rotary and vertical position of the movable pipette tip 6 relative to the lower tray 17 with segmented chambers 31, 32, 33, containing the reagents.

The movable pipette tip 6 can be aligned, by pre-determined programming of the instrument 3 and in particular the control of the central drive coupling 35, above the desired fixed part of the pipette 8 and lowered into the chamber 31, 32, 33, breaking through a breakable seal 11 (if this has not already been broken). The mechanical coupling of the moveable pipette tip 6 and the fixed pipette portion 8, together with the pneumatic connection to the instrument allows fluid to be aspirated or dispensed from or to selected chambers 31, 32, 33 within the lower tray 17 or the reaction chamber 22.

Some of the sample preparation process steps are highly sensitive to carry-over of fluid residue from previous transfer steps, consequently, the lower tray 17 includes an area 51 containing wadding, paper or other means, such as mould texture or pattern, that the movable pipette tip 6 can be lowered onto, to remove excess residue from the pipette tip 6.

The internal volume of the movable pipette reservoir 18 and the programmable pneumatic system ensures that fluid can be transferred by the movable pipette 6 without the need for liquid to flow through the passageway 16 of the movable pipette's central shaft 5, into the instrument 3. A filter 15 between the movable pipette reservoir 18 and pneumatic supply prevents airborne particles from the cartridge 1 contaminating the pneumatic system within the instrument 3.

To prevent air lock within the chambers 31, 32, 33, the movable pipette tip 6 includes a piercing member such as a spike 12 that pierces the selected chambers breakable seal 11 prior to movable pipette tip 6 engaging with the 'fixed' part of the pipette 8. The spike's 12 function is to provide a vent through the breakable seal 11 and as such it is located away from the movable pipette tip 6. The vent may be achieved by rotary movement of the movable pipette 6 to form an elongated hole that does not seal around the spike 12. Alternatively, the geometry of the spike 12 can be non-circular so as to prevent it sealing against the breakable seal 11 during insertion.

A filtered breather vent 51, shown here as comprised within the upper cover 27 ensures that the pressure in the cartridge 1 can equalise with ambient during operation. This prevents the risk of the cartridge 1 becoming pressurised and potentially contaminating the instrument 3. The filtered breather vent 51 can be held in place, for example, by an identification label 50.

Mixing of fluids within chambers 31, 32, 33 can be promoted by repeatedly aspirating and dispensing fluid into the pipette tip 6 so as to cause rapid fluid movement within the chamber 31, 32, 33. This yields fast and comprehensive mixing at lower overall system cost than the possible alternatives such as vibrating or agitating the cartridge 1.

The pipetting arrangement allows for a solution of paramagnetic particles or beads 54 to be used to capture nucleic acid in the sample, and the paramagnetic particles 54 can be subsequently washed to remove unwanted substances whilst retaining the nucleic acid for subsequent treatment or release, according to methods well-known in the art.

Advantageously, the arrangement assumes a fixed location and includes two magnets 53, movable between a first position, where their magnetic field attracts magnetic particles to surfaces of the chamber 31, 32, 33, and a second position, where its magnetic field has substantially no effect on the magnetic particles.

When in their first position, the magnets 53 are mounted perpendicular to either side of the V shaped chamber 31, 32, 33 to provide a concentrated magnetic field 59 at either side of the chamber and a neutral 'particle free' plane 63 between them that allows fluid, without magnetic particles, to be removed from the lowest point in the chamber 31, 32, 33, via a fixed pipette 8.

Pipetting clear fluid from the neutral 'particle free' plane 63 allows other areas of the fluid to be bought closer to the rapid clearing zone. This arrangement can significantly increase the rate of bead capture and provides a substantial speed and efficiency benefit over prior art approaches.

Although cartridge 1 can be individually configured for specific sample and test types, some of the fluids and substances stored in the chambers 31, 32, 33 in the lower tray 17 are common to several sample types. Cost-efficiencies and shelf-life advantages may be achieved with a generic cartridge 1 that comprises just these common materials. Others might vary for different preparations and these may advantageously be provided in a separate plug-in cartridge 20, inserted into the lower tray 3, prior to use. The plug-in cartridge 20 contains a plurality of chambers 55 suitable for storing solid, dried or liquid substances and can be covered by a breakable cover seal 57, such as a foil seal or the like to prevent spillage in transit and increase the shelf life of the reagents. The plug-in cartridge 20 also contains a plurality a fixed nozzles 56 that combine with the movable pipette 5.

The plug-in cartridge 20 can be stored in a separate foil pouch, away from the liquids within the cartridge 1, which provides the benefit of longer shelf life for dried or solid reagents. The plug-in cartridge 20 can carry a machine-readable identification coded tag 58, such as a 2D bar code 50, RFID chip or other optical, magnetic or near-field wireless interface for conveying data that can be read by the reader. Coded tag 58 can convey data identifying the customised nature of the cartridge 1 incorporating the plug-in cartridge 20 including identification of the assays, steps and/or tests contained within. The coded tag can convey specific instructions to the instrument 3. For example a plug-in cartridge 20 comprising materials for a new sample and/or test may be launched on the market after the introduction of the system and the coded tag can be used to advise the instrument 3 of specific requirements, for example temperature cycling requirements. Alternatively or additionally the coded tag may be used to advise the instrument of time periods, such as settling times during sample aspiration for example. The coded tag may further convey traceability and/or tracking information as well as other useful parameters such as expiry date. The data and instructions encoded on the coded tag may be used automatically by the instrument 3, and may be done so selectively either with or without user intervention, to deliver a number of enhanced system benefits, safety and efficacy warnings, and/or usability features.

The cartridge geometry allows the plug-in cartridge 20 to be snapped into the lower tray 17, to form part of the chemistry set, accessible by the movable pipette tip 6, required to prepare the sample. Dried or solid reagents are hydrated, during operation, using the aqueous substances stored in the other chambers in the cartridge.

Once the sample has been processed, the analyte can be transferred from a chamber 31, 32, 33, using the movable pipette 6, to a reaction vessel 22 for suitable reaction, such as thermocycling for PCR.

The reaction vessel 22 is constructed from a moulded section 64, a flexible film 65 and a semi breathable vent 66. Fluid is transferred from a selected chamber 31, 32, 33 and is introduced into the reaction vessel 22 via the movable pipette tip 6. Bubbles in the reaction fluid can affect the analysis readings and the reaction vessel is designed with a geometry that ensures that bubbles are not formed during fill. A breather filter allows air to escape from the reaction vessel 22 during the fill process; however the filter is manufactured using hydrophobic material that does not allow fluid through it at the relatively low pressures provided by the instrument 3. In this way, the movable pipette tip 6 is able to produce a positive pressure in the cuvette during the reaction process which helps its thermal contact with the thermal block.

Measurement of the fluid 10 in the reaction vessel 22 can be achieved via conventional methods such as optical means, electrochemical means, electrophoresis and custom chips. In all cases the instrument interfaces with the cartridge, either optically, through transparent walls in the reaction chamber or electrically, through electrodes via pads on the cartridge.

Figure 27:
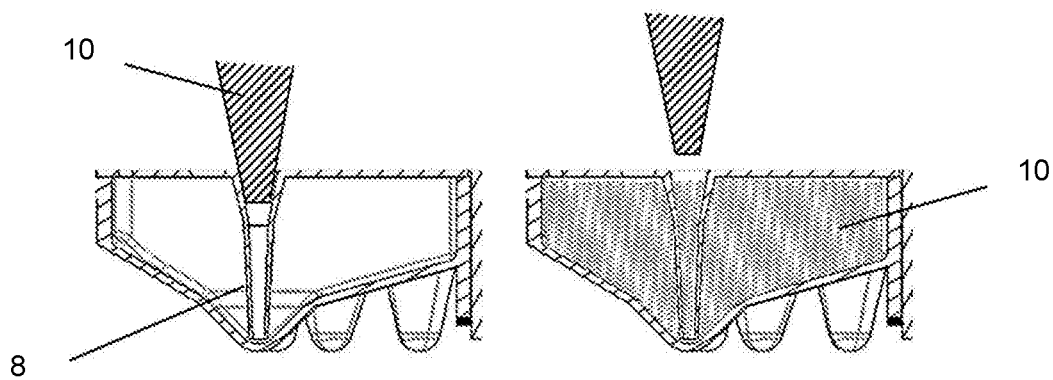
FIG. 27 illustrates a filling process provided by the current invention.

As shown in FIG. 27, the arrangement allows the chambers 31, 32, 33 to be filled with liquid reagents 10, through the pipette tip, via the fixed part of the pipette 8. Advantageously, this means that it is possible to fill and foil seal the chamber with virtually no head space, thus preventing the risk of fluid hang up in non accessible areas of the chambers 31, 32, 33 which can result in lower than expected fluid transfer that can potentially lead to poor DNA extraction.

The cartridge has been described as comprising a pipette structure that has a moving part 6 and fixed parts 8. It should be apparent that this approach yields substantial improvements in form factor, in that the cartridge 1 can achieve a significantly lower profile than if a single-piece, movable pipette were used. However, if space is not a constraint, then the movable pipette 6 can be extended such that the movable tip has sufficient length to be inserted down to the lowest point of each chamber 30, 31, 32, 55 and thus the fixed parts 8 can be eliminated from the system. This might reduce overall cost at the expense of increasing the length of central shaft 5, drive shaft 35 and the overall height of the cartridge 1.

The arrangement of the movable pipette tip 6, fixed chambers 31, 32, 33 and reagent cartridge 20 allows for a highly flexible and programmable approach that can be used for many types of diagnostic process such as Quantitative or real time PCR (thermally cycled), PCR (isothermal), immunoassay, clinical chemistry, lateral flow, and many others where samples are transferred, mixed, reacted and analysed.

With the invention a user places the sample (blood, fluid, etc.) into the sample preparation cartridge 1 and then places it in the analytical reader 3. The reader 3 engages with the sample preparation cartridge 1 (for example mechanically, pneumatically, optically, or thermally) and processes the sample in the cartridge. At the end of the processing, the reader measures the sample preparation cartridge (this could be optical or electrical) and provides a result to the user. The sample preparation cartridge 1 is then removed from the reader of the sample preparation device 3 and can be disposed of.

A compact embodiment has been disclosed wherein the cartridge is inserted in an analytical reader for processing.

Alternative attachment methods and topologies will be readily apparent to the skilled person, including placing the cartridge onto an analytical instrument, or engaging the analytical reader's drive member into the cartridge using bayonet-like features.

As will be appreciated from the above, the present invention provides a simple low cost sample preparation cartridge 1 which is easy for an operator to use through simple insertion. By use of the two-part pipette configuration the overall depth of the sample preparation cartridge 1 can be reduced to keep it small and compact, low cost and easy to handle. Furthermore, by the use of filtering in the conduits of the analytical reader 3 it is possible to ensure that there is no contamination of the core analytical reader within a sample preparation device or instrument by individual samples whilst still ensuring simple operation.

The invention claimed is:

1. A sample preparation cartridge for use with a sample preparation device, the cartridge comprising:
    a housing defining a plurality of separate segments containing analytes, beads, or analytes and beads in use; and
    a moveable pipette positioned above the plurality of separate segments, wherein the pipette is arranged to transfer, in use, analytes, beads, or analytes and beads from one segment of the plurality of segments to another segment of the plurality of segments in order to prepare a sample for analysis;
    wherein the pipette comprises:
    a reservoir section capable of supporting fluids, and a nozzle section capable of dispensing and aspirating fluids including the analytes, beads, or analytes and beads from the plurality of segments;
    wherein the plurality of segments are arranged around a central axis of the housing and the moveable pipette is arranged to rotate around the central axis and lower towards, or raise from, a desired segment of the plurality of segments when it has been rotated to be positioned above the desired segment of the plurality of segments.

2. The sample preparation cartridge according to claim 1, wherein at least one of the plurality of segments has a fluid seal and the moveable pipette further comprises a piercing component arranged to pierce the fluid seal when the pipette is moved to the at least one respective segment.

3. The sample preparation cartridge according to claim 1, further comprising a shaft attached to the pipette and positioned at the central axis, the shaft being arranged to engage, in use, with a drive member in an analytical reader of the sample preparation device when the sample preparation cartridge is inserted therein so that the drive member can rotate the shaft and raise and lower the pipette, the shaft comprising a passageway for allowing fluid communication between the pipette and the analytical reader.

4. The sample preparation cartridge according to claim 3, wherein the shaft further comprises a vent to allow an interior of the housing to be balanced to atmospheric pressure.

5. The sample preparation cartridge according to claim 1, wherein the pipette is pneumatically connected to a programmable control system for providing a positive and negative flow of air through the pipette in use, to provide the dispensing and aspirating of fluids from the plurality of segments through the pipette.

6. The sample preparation cartridge according to claim 1, wherein at least one segment of the plurality of segments contains reagents and at least one segment of the plurality of segments contains paramagnetic beads.

7. The sample preparation cartridge according to claim 6, wherein the segment containing paramagnetic beads has a tapering V-shaped floor so as to provide a drainage point to extract fluids.

8. The sample preparation cartridge according to claim 6, further comprising:
    an arrangement of magnets moveable to a position, in use, where a magnetic field of the arrangement of magnets attracts the paramagnetic beads to a plurality of surfaces of the at least one segment, the arrangement of magnets and the at least one segment being arranged such that they can be used to provide a zone clear of paramagnetic beads for the pipette to aspirate fluid from the at least one segment; and that by aspirating fluid from the at least one segment thus, bringing the paramagnetic beads closer to the magnetic field and increase the rate of paramagnetic bead capture.

9. The sample preparation cartridge according to claim 1, further comprising a coded tag.

10. The sample preparation cartridge according to claim 9, wherein the coded tag comprises a communication interface operable to convey real time information between the sample preparation cartridge and an instrument into which the sample preparation cartridge can be removably inserted.

11. The sample preparation cartridge according to claim 1, wherein at least one of said segments of the plurality of segments comprises a fixed section of a pipette component and the moveable pipette comprises a nozzle, the pipette being configured, in use, to be moved between a position in which the nozzle is in sealed engagement with the fixed section of pipette component and a position in which nozzle is positioned adjacent to another segment of said plurality of segments.

12. A sample preparation cartridge for use with a sample preparation device, the cartridge comprising:
    a housing defining a plurality of separate segments, at least one of said plurality of segments comprising a fixed section of a pipette component; and
    a moveable pipette arm comprising a pipette tip, the pipette arm being configured to be moved between a position in which the pipette tip is in sealed engagement with the fixed section of the pipette component and a position in which pipette tip is positioned adjacent to another segment of said plurality of segments; wherein
    the plurality of segments are arranged around a central axis of the housing and the moveable pipette arm is arranged to rotate around the central axis and lower towards, or raise from, a desired segment of the plurality of segments when it has been rotated to be positioned above the desired segment of the plurality of segments.

13. The sample preparation cartridge according to claim 12, wherein at least one of the segments of the plurality of segments has a fluid seal and the moveable pipette arm further comprises a piercing component arranged to pierce the fluid seal when the pipette arm is moved to the at least one respective segment.

14. The sample preparation cartridge of claim 13, wherein the pipette arm is configured to provide a rotary movement such that the piercing component can produce an elongated hole that does not seal around the piercing component in use.

15. The sample preparation cartridge according to claim 12, further comprising a shaft attached to the pipette arm and positioned at the central axis, the shaft being arranged to engage, in use, with a drive member in an analytical reader of the sample preparation device when the sample preparation cartridge is inserted therein so that the drive member can rotate the shaft and raise and lower the pipette arm, the shaft comprising a passageway for allowing fluid communication between the pipette arm and the analytical reader.

16. The sample preparation cartridge of claim 12, wherein the pipette tip is configured to aspirate and dispense fluids, and the fixed section of the pipette component provides a fluid path into the at least one respective segment.

17. The sample preparation cartridge according to claim 12, wherein at least one segment of the plurality of segments contains reagents and at least one segment of the plurality of segments contains paramagnetic beads.

18. The sample preparation cartridge according to claim 12, further comprising a coded tag.

19. The sample preparation cartridge according to claim 18, wherein the coded tag comprises a communication interface operable to convey real time information between the sample preparation cartridge and an instrument into which the sample preparation cartridge can be removably inserted.

20. The sample preparation cartridge according to claim 12, wherein each of the plurality of segments have a respective fixed section of a respective pipette component.

* * * * *